US008425227B2

(12) United States Patent
Marotta

(10) Patent No.: US 8,425,227 B2
(45) Date of Patent: Apr. 23, 2013

(54) ACCURATE ANALOGS FOR PROSTHESIS USING COMPUTER GENERATED ANATOMICAL MODELS

(76) Inventor: Leonard Marotta, West Islip, NY (US)

( * ) Notice: Subject to any disclaimer, the term of this patent is extended or adjusted under 35 U.S.C. 154(b) by 45 days.

(21) Appl. No.: 12/931,705

(22) Filed: Feb. 8, 2011

(65) Prior Publication Data
US 2011/0129800 A1    Jun. 2, 2011

Related U.S. Application Data

(63) Continuation of application No. 11/973,747, filed on Oct. 10, 2007, now Pat. No. 7,887,327, which is a continuation-in-part of application No. 11/449,461, filed on Jun. 8, 2006, now Pat. No. 7,281,927, which is a continuation of application No. 10/056,101, filed on Jan. 24, 2002, now Pat. No. 7,059,856.

(60) Provisional application No. 60/316,832, filed on Aug. 31, 2001, provisional application No. 60/402,187, filed on Aug. 10, 2002.

(51) Int. Cl.
*A61C 19/04* (2006.01)
(52) U.S. Cl.
USPC .................. 433/72; 433/213; 606/96
(58) Field of Classification Search ............. 433/72, 433/75, 76, 213; 606/96; 623/17.19
See application file for complete search history.

(56) References Cited

U.S. PATENT DOCUMENTS

| | | | |
|---|---|---|---|
| 2,745,180 A | 5/1956 | Kiernan, Jr. | |
| 2,857,670 A | 10/1958 | Kiernan, Jr. | |
| 3,981,079 A | 9/1976 | Lenczycki | |
| 4,331,423 A | 5/1982 | Yanney, Jr. | |
| 4,368,042 A | 1/1983 | Felstead et al. | |
| 4,447,209 A | 5/1984 | Sutter | |
| 4,708,654 A | 11/1987 | Branemark | |
| 4,713,004 A | 12/1987 | Linkow et al. | |
| 4,832,601 A | 5/1989 | Linden | |
| 4,955,811 A | 9/1990 | Lazzara et al. | |

(Continued)

FOREIGN PATENT DOCUMENTS
WO     WO98/52490     11/1998

OTHER PUBLICATIONS

San Diego Radiology Imaging Center, "SimPlant Dental Imaging CT Scan", 2007 pp. 1-3 from website of northcountyrad.com.

(Continued)

*Primary Examiner* — Ralph Lewis
(74) *Attorney, Agent, or Firm* — Alfred M. Walker

(57) ABSTRACT

Pre-surgical planning for cranial and facial reconstruction includes preparing a computer generated jaw or skull model for determining a locational position for a dental implant, a surgical bone implant to repair missing bone in the cranium, install ear prostheses, and/or install nose prostheses. The computer generated jaw or skull model is made from medical imagery and computer aided design. A surgical guide is prepared with oversize holes in registration with analogs for the dental or surgical bone implants to be inserted in the jaw or cranial skull model. The surgical guide is fitted atop each analog, and bonded to the jaw or skull model at a predetermined angle of the analog in the jaw or skull. The surgical guide is removed and attached to the jaw or skull of a patient for accurate drilling for insertion of the implants into the jaw or skull of the patient.

8 Claims, 11 Drawing Sheets

U.S. PATENT DOCUMENTS

| | | | |
|---|---|---|---|
| 4,961,422 A * | 10/1990 | Marchosky et al. | 607/99 |
| 4,988,298 A | 1/1991 | Lazzara et al. | |
| 5,013,242 A | 5/1991 | Prezmecky | |
| 5,030,094 A | 7/1991 | Nardi et al. | |
| 5,066,224 A | 11/1991 | Block et al. | |
| 5,092,771 A | 3/1992 | Tatum, III | |
| 5,108,288 A | 4/1992 | Perry | |
| 5,125,841 A | 6/1992 | Carlsson | |
| 5,156,777 A * | 10/1992 | Kaye | 264/40.1 |
| 5,201,737 A * | 4/1993 | Leibinger et al. | 606/284 |
| 5,221,206 A | 6/1993 | Nardi | |
| 5,302,125 A | 4/1994 | Kownacki et al. | |
| 5,368,483 A | 11/1994 | Sutter et al. | |
| 5,413,480 A | 5/1995 | Musikant et al. | |
| 5,433,607 A | 7/1995 | Schmid et al. | |
| 5,456,723 A | 10/1995 | Steinemann et al. | |
| RE35,263 E | 6/1996 | Silva et al. | |
| 5,542,847 A | 8/1996 | Margulies | |
| 5,556,278 A * | 9/1996 | Meitner | 433/75 |
| 5,564,921 A | 10/1996 | Marlin | |
| 5,564,922 A | 10/1996 | Rosa et al. | |
| 5,564,924 A | 10/1996 | Kwan | |
| 5,569,250 A * | 10/1996 | Sarver et al. | 606/281 |
| 5,658,147 A | 8/1997 | Phimmasone | |
| 5,674,073 A | 10/1997 | Ingber et al. | |
| 5,697,779 A | 12/1997 | Sachdeva et al. | |
| 5,704,788 A | 1/1998 | Milne | |
| 5,725,376 A * | 3/1998 | Poirier | 433/172 |
| 5,752,962 A * | 5/1998 | D'Urso | 606/130 |
| 5,762,500 A | 6/1998 | Lazarof | |
| 5,766,009 A | 6/1998 | Jeffcoat | |
| 5,768,134 A | 6/1998 | Swaelens | |
| 5,769,630 A | 6/1998 | Hoffman | |
| 5,782,918 A | 7/1998 | Klardie et al. | |
| 5,827,062 A | 10/1998 | Driskell et al. | |
| 5,829,981 A | 11/1998 | Ziegler | |
| 5,836,768 A | 11/1998 | Huskens et al. | |
| 5,882,200 A | 3/1999 | Sutter et al. | |
| 5,904,483 A | 5/1999 | Wade | |
| 5,934,906 A | 8/1999 | Phimmasone | |
| 5,947,733 A | 9/1999 | Sutter et al. | |
| 5,989,026 A | 11/1999 | Rogers et al. | |
| 6,039,568 A | 3/2000 | Hinds | |
| 6,068,478 A | 5/2000 | Grande et al. | |
| 6,102,702 A | 8/2000 | Folsom, Jr. et al. | |
| 6,116,904 A | 9/2000 | Kirsch et al. | |
| 6,120,292 A | 9/2000 | Buser et al. | |
| 6,126,445 A | 10/2000 | Willoughby | |
| 6,142,782 A | 11/2000 | Lazarof | |
| 6,159,010 A | 12/2000 | Rogers et al. | |
| 6,213,773 B1 | 4/2001 | Gittleman | |
| 6,227,856 B1 | 5/2001 | Beaty et al. | |
| 6,254,639 B1 * | 7/2001 | Peckitt | 623/11.11 |
| 6,261,097 B1 | 7/2001 | Schmutz et al. | |
| 6,309,215 B1 | 10/2001 | Phan et al. | |
| 6,312,259 B1 | 11/2001 | Kvarnstrom et al. | |
| 6,332,777 B1 | 12/2001 | Sutter | |
| 6,508,650 B2 | 1/2003 | Gittleman | |
| 6,688,887 B2 | 2/2004 | Morgan | |
| 6,799,970 B2 | 10/2004 | Martin et al. | |
| 7,018,207 B2 | 3/2006 | Prestipino | |
| 7,059,856 B2 | 6/2006 | Marotta | |
| 7,281,927 B2 | 10/2007 | Marotta | |
| 7,747,305 B2 * | 6/2010 | Dean et al. | 600/407 |
| 7,887,327 B2 * | 2/2011 | Marotta | 433/213 |
| 8,135,492 B2 * | 3/2012 | Yau et al. | 700/182 |
| 2005/0133955 A1 | 6/2005 | Christensen | |
| 2006/0291968 A1 * | 12/2006 | Greenberg | 408/202 |
| 2008/0255582 A1 * | 10/2008 | Harris | 606/129 |

OTHER PUBLICATIONS

Medical Modeling, "CT Based Anatomical Modeling", 2007 pp. 1-3 from website of "medicalmodeling.com".

Milwaukee School of Engineering (MSOE), "What is Solid Freeform Fabrication", 2007 pp. 1-5.

Medical Modeling, AccuDental Guided Implantation, 2007 pp. 1-2.

* cited by examiner

ACCURATE ANALOGS FOR PROSTHESIS USING COMPUTER GENERATED ANATOMICAL MODELS

RELATED APPLICATIONS

This application is a continuation of application Ser. No. 11/973,747 filed Oct. 10, 2007 now U.S. Pat. No. 7,887,327, which application is a continuation in part of application Ser. No. 11/449,461, filed Jun. 8, 2006, now U.S. Pat. No. 7,261,927 and claims priority under 35 U.S.C. 120 therefrom, which application is a continuation of application Ser. No. 10/056,101, filed Jan. 24, 2002, now U.S. Pat. No. 7,059,856 and claims priority under 35 U.S.C. 120 therefrom, which application claims benefit under 35 U.S.C. 119 (e) of provisional application Ser. No. 60/316,832 filed Aug. 31, 2001 and provisional application Ser. No. 60/402,187 filed Aug. 10, 2002.

FIELD OF THE INVENTION

This invention relates generally to the construction of a dental or cranial prosthesis that is attached to an implant in the bone of a person's jaw or skull.

BACKGROUND OF THE INVENTION

Dental implants are a common treatment for the replacement of a missing tooth or missing teeth. An implant is placed into the bone in a person's jaw in a variety of fashions and using a variety of systems. The bone and the implant adhere together in a process known as osseointegration, thus enabling a person to have a new tooth or set of teeth held into position in the jaw utilizing screws to hold them down.

Many firms manufacture complete systems of dental implants and prosthetic components for subsequent attachment to the implant. In a typical construction, the implant has an axially threaded hole at its top, that is, the proximal end, near the gum surface. After the implant has integrated with the bone, the gum of the implant is opened to expose the tapped hole. Then a transmucosal abutment is attached to the tapped hole of the implant and extends to a level above the gum or substantially to the gum surface. The protruding free end of the abutment is constructed for attachment of a prosthesis. For preventing rotation of the prosthesis, the protruding end of the abutment requires a non-round shape and a hexagon protrusion has been widely used. A recessed hexagon is also popular with some systems. The abutment also includes a central threaded hole concentric with the threaded hole of the implant and extending inward toward the jaw bone.

A false tooth or frame is provided with a hole therethrough, known in the industry as a chimney, and a non-round recess in its base corresponds in shape to the protruding non-round cross section for the abutment. Thereby, the crown can be connected to the abutment and relative rotation between them is prevented so long as critical contours of the abutment and the recess in the crown are maintained.

To prevent the crown or bridge from lifting axially from the abutment, a final screw is passed into the chimney opening and engages the tapped hole in the implant by way of the abutment so as to hold the crown axially to the abutment and to the implant. Thus, the crown cannot rotate about the abutment or implant because it is mated with the special contours on the exposed end of the abutment. The abutment is similarly mated to the proximal or outer end of the implant. The crown cannot pull away from the abutment when the screw has been tightened into place.

Finally, the chimney above the screw is filled with a composite material that hardens and is shaped as part of the crown to look lie a natural tooth.

There are many variations in construction.

In an alternative method, the crown is attached directly to a non-round protrusion of the implant and is held directly to the implant by a gold screw without use of an intermediate abutment.

The implant is intended to be a permanent fixture in the jaw bone. The abutment and crown may be replaced if necessary due to damage or poor fit by gaining access to the screw head by way of the chimney, and backing off the screw so that the crown and abutment or crown to the implant can be separated from the implant. Thus repairs may be made of an abutment and crown with no or little inconvenience.

Therefore, the fit of an implant with the crown or frame must be perfect. If a prosthesis is placed into the mouth and does not seat correctly, the implant or abutment can be damaged. If an implant is damaged there are not many options for its repair. In cases where there have been a poor fit, the screws have broken inside the abutment requiring the replacement of the abutment. There have been cases where the screw broke inside the implant. The implants cannot be replaced without surgically removing them. Placing a new implant in the same spot is not an advised option.

Among related patents disclosing dental analogs include U.S. Pat. No. 6,142,782 of Lazarof, which shows a dental analog with annular wings. However, the annular wings do not hinder rotating and therefore misplacement of the analog within the replica cast stone. The annular wings of Lazarof do not intersect with the cast stone material enough to prevent rotation.

An alternative method for making dental prostheses that does not involve making an impression of the patient's mouth has been recently introduced. It is based on Solid Freeform Fabrication (SFF) which is an industrial prototyping technique whereby 3-D Computer Aided Design (CAD) files describing a part are used to guide the actual fabrication of a solid object by one of a variety of additive methods such as stereolithography, laminated object manufacturing, or fused deposition modelling. U.S. Pat. No. 6,978,188 of Christensen as well as his published patent application 2005/0133955 illustrate how CT scans or MRI scans can be substituted for CAD input to create the files necessary to drive a stereolithography system which can then be used to model human bone features. Medical Modeling LLC has used such a method in their AccuDental™ system to create dental prostheses. Prior to implantation of posts, a scan is made of a patient's jaw. This data is used to create files resulting in an accurate solid translucent resin model of a patient's jaw. Teeth and roots are rendered in a different hue to show clearly how the teeth are anchored in the jaw bone. A dental surgeon then indicates on the jaw model where analogs are to be placed in the model and at what angle they should be inserted. Holes are then drilled into the jaw model to accept the analogs. A surgical guide is thermally formed on top of the implant region of the model engaging the teeth or ridge surface with a close fit and transferring the analog positions accurately. Alternatively, computer generated surgical guides which fit onto a jaw model are used. Surgical guide sleeves at the appropriate angle are then bonded at the analog sites onto the surgical guide. The surgical guide is snapped off the teeth or ridge surface of the model and will be transferred to the patient's mouth and snapped onto the actual teeth or the ridge surface thereby providing accurate guides for drilling the holes for the actual implants while at a remote lab, the prosthesis is being fabricated using the analogs in the jaw model. Surgical guides fit not only on teeth, but can be used on totally edentulous jaws as well engaging soft tissue or bone surface as represented on the jaw model and on the actual patient jaw.

OBJECTS OF THE INVENTION

Accordingly, it is the object of the invention to provide a method for insuring the most accurate seating possible of a prosthesis to an abutment or implant in the jaw or skull of a patient.

SUMMARY OF THE INVENTION

The present invention comprises an implant analog that may include a standard abutment that can be mounted in the dental lab replica of the relevant section of a patient's mouth more securely than heretofore possible. Because of the inventive implant analog, dental labs can now create a crown that will attach more accurately to the implant in the patient's mouth. The analogs of the present invention are desirably longer than the analogs used heretofore and have a pin that projects from the base of the analog. Desirably, the inventive analogs have a side ridge. Moreover, the analog has substantially the same height and dimensions as a conventional implant and abutment. In a preferred embodiment, the analog of the present invention is formed from stainless steel.

A careful confidential experiment was conducted at New York University of School of Dental Medicine by Dr. C. Jager, Dr. G. R. Goldstein, Dr. E. Hittelman and the Applicant herein. The experiment was designed to compare the performance of a prior art analog of NOBEL BIOCARE®, as shown in FIG. 9, to that of one embodiment of the present invention, as shown in FIG. 4. A statistically significant improvement for the present invention was found in terms of framework fit. Also, resistance to applied torque was found to be significantly improved for the analog of this invention.

The experiment evaluated torque prostheses to laboratory dental implant analogs. The study evaluated the movement of the prior art analog of NOBEL BIOCARE®, as shown in FIG. 9, and the embodiment shown in FIG. 4 of the present invention. Both were torqued to 20 Ncm in a reinforced type IV die stone. 80 analogs were divided into groups of 4 analogs, including three of the prior art analog shown in FIG. 9 with one of the present invention shown in FIG. 4. These analogs were embedded in thirty equal blocks of Type IV plaster stone using a prefabricated four unit implant framework. Of the twenty analogs, ten were imbedded in the stone at a depth of four cm and ten were imbedded at a depth of six cm from the implant platform. These groups of ten were then divided into groups of five each, where five of the prior art analogs shown of the present invention in FIG. 9 were torqued to 20 Ncm in each group and five analogs shown in FIG. 4 were torqued to 20 Ncm. The initial framework was used to evaluate the fit of each analog therein. In the 4 mm depth group of the prior art shown in FIG. 9, two of the five samples (40%) did not allow the framework to fit the analog. In the 6 mm depth of the prior art analogs shown in FIG. 9, three of the five samples (60%) did not allow the framework to fit. However, all of the dental analogs shown in FIG. 4 of the present invention fit back to the cast.

As a result, the analogs of the present invention, as shown in FIG. 4, were able to resist movement within a stone cast when torqued, unlike a significant portion of the prior art dental analogs shown in FIG. 9.

Therefore, the dental analogs of the present invention have unexpected, beneficial results not achievable with the dental analogs of the prior art shown in FIG. 9.

A method of preparing dental crowns efficiently and accurately, includes the steps of:

a. preparing an analog for a jaw implant supporting a dental crown mounting pin having at least one anti-rotation anchoring projection extending discretely and radially from said pin adjacent a bottom end thereof;

b. inserting bottom-end-down said prepared mounting pin into a dental crown casting mold;

c. securing said prepared mounting pin temporarily in place within said casting mold;

d. adding settable plaster or plastic molding material to said casting mold so as to embed said bottom end of said pin by surrounding said bottom end of said pin with said plaster or plastic molding material;

e. allowing said plastic molding material to set and harden with said prepared pin embedded within said molding material; and f. utilizing said embedded mounting pin to make a dental crown.

Regarding the alternative method described in the previous section using a resin model of a patient's jaw, the analogs used must be resistant to pull-out and rotation as in the method using the stone plaster method. Whether the resin model is a product of stereolithography or otherwise fabricated, it is drilled to accept an analog post. The alternate embodiment of this invention describes analog posts with features for robustly grasping the side walls of these retaining holes in the resin model. Clearly, transverse or radially protruding features cannot be appended to the analog posts since these would not be compatible with insertion.

The first alternate embodiment uses a single axially attached rod or wing on the lower portion of the analog post. The post is then forced into a slightly undersized hole and resists both twisting and pull-out. A second embodiment using axial rod features uses two such rods on opposite sides of the analog post. A third such embodiment uses three such rods attached every 120 degrees around the bottom end of the post. Any number of such rods can be attached preferably in a symmetric array. The rods can also be enhanced in their gripping action by texturizing their outer surface; alternatively, axial grooves along their length at their outermost position can be added.

Another embodiment of analog post for hole engagement is made of a larger diameter with a tapered top; a regular array of longitudinal grooves or flutes on the outer side surface engage the hole sides. Yet another embodiment of analog post is one with a knurled outer surface and an annular groove near the bottom end. A final embodiment has male threads along the analog shank which permit screwing into the hole in the resin model much akin to the thread-forming action of a wood screw in a pilot hole in wood.

When using model based presurgical planning techniques, computer based stereolithography or non-computer methods are used to create an accurate jaw model of resin, plaster, or "stone" or other plastic material. Similarly, surgical guides which form fit onto the jaw model and onto the patient's jaw are also created. Once analogs are inserted into the jaw model, surgical guide sleeves are bonded to the surgical guide at the analog sites using cement or adhesive inside oversized holes in the surgical guide. These must be at the appropriate height, and the orientation must match that of the analogs in the jaw model. Another embodiment of this invention is a set of accessory parts and a method to insure that the alignment of the surgical guide sleeves bonded to the surgical guide will match that of the analog in registration.

After the analogs are inserted in the jaw model, at each analog site attachments to each analog are made which will orient the surgical guide sleeve rigidly and accurately to represent the orientation of the analog. After all the surgical guide sleeves are thereby attached to the analogs, the surgical guide with oversize holes at each analog site is lowered onto the jaw model and all surgical guide sleeves are bonded to the surgical guide while they are still attached to the analogs. After the cement or adhesive sets, screws are removed from each analog to free the surgical guide with all of the surgical guide sleeves accurately attached. The guide is then used inside the patient's mouth to drill accurate implant holes by using each of the surgical guide sleeves as drill guides.

The parts attached to each analog in the jaw model are a surgical guide sleeve supported by a form-fitting cylinder support mount, a tube adapter to adjust the height of the guide sleeve above the analog (if necessary), and a screw threaded through the three parts from the top to secure the assembly to the analog below.

Presurgical planning techniques using accurate whole skull models or models of skull portions other than jaws are also used for cranial and facial reconstruction. Attachments use surgical implants in bone. For example such an approach is used to repair missing bone in the cranium, ear prostheses, and nose prostheses. The procedure starts with an accurate model and a surgical guide with oversize holes in registration with the analogs inserted at sites determined by a surgeon on the skull model. Using the procedure and analog attachments as described above for dental implants, appropriately sized tube adapters, cylinder support mount, surgical guide sleeve and attachment screw are attached to each analog in the skull model. The surgical guide is then fitted carefully atop the protruding elements atop each analog, and the surgical guide sleeves are cemented or otherwise bonded within the oversize holes of the guide capturing the precise angle of the analog in the model. The analog screws are then removed releasing the surgical guide with guide sleeves attached for accurate drilling during the surgical procedure for insertion of the implants.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Simplified, the construction of the prosthesis begins after the osseointegration of the implant with the dentist making an impression of the relevant section of the patient's mouth. When constructing the prosthesis, the dentist makes an impression including an impression coping. Desirably, the impression material employed is hard and elastic when set, such as the materials sold under the trade names IMPRAGUM, EXPRESS and PRESIDENT.

Once the impression material hardens, the tray containing the impression is sent to a dental lab where the prosthesis is made. The dental lab uses this impression to make a replica of the relevant section of the patient's mouth. Typically, the replica is made of gypsum to form plaster, and is made to reproduce the milieu into which the prosthesis is to fit, including, for example, any hexagonal protrusion or recession in the abutment the dentist is using. Alternately, the replica can also be made of plastic, such as resin.

Figure 1:
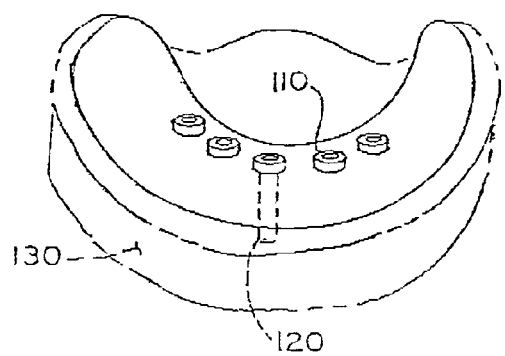
FIG. 1 is a view of a dental lab replica showing the position of an analog and an abutment.

For example, FIG. 1 shows a view of dental lab replica 130 with analog 120 and abutment 110.

Figure 2:
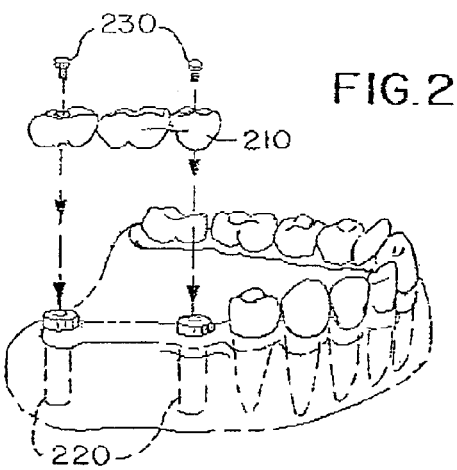
FIG. 2 is a view of a lower jaw about to receive a prosthesis and having two implants.

Moreover, FIG. 2 shows an actual patient lower jaw with two implants 220, a three tooth prosthesis 210 and screws 230 to retain prosthesis 210 in implants 220.

In making the impression, the impression coping is attached to the implant in the same way the final prosthesis will attach. The impression coping rests flush on top of the implant, or implant and abutment, with a guide screw passing through and into the implant. The impression coping remains in the impression in the same position that was in the mouth and the guide screw must be removed before the impression can be removed from the patient's mouth.

In making the dental lab jaw model, or replica, the analog is attached to the impression coping with a guide screw going through the impression coping and into the analog. All of the teeth in the relevant portion of the mouth are replicated in the model, which desirably is made of gypsum. The goal is to have the analog in the replica in the position that corresponds to the position of the implant in the patient's mouth, including the orientation of any protrusion or recess.

The present day tools offered by the implant manufacturers utilize brass or stainless steel analog.

The configuration of the prior art analogs replicates the internal thread dimension of the implant or abutment and copies the shape of the external or internal hexagon. However, the outside diameter of a prior art analog maintains a shape that is not consistent with the needs of the dentist or technician in constructing the prosthesis. Conventional analogs are too small and are removed from the gypsum model too easily. Moreover, the exterior surface of conventional analogs are too smooth which permits the analog, and thus the prosthesis, to rotate in the model during construction of the prosthesis. Such rotation moves the hexagonal position of the prosthesis into a position that does not match the corresponding position of the implant in the patient's mouth.

Figure 3:
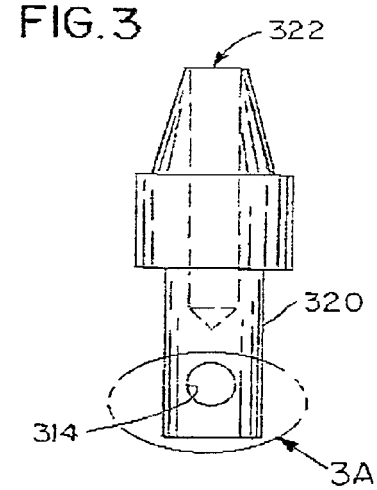
FIG. 3 is a view of an embodiment of the present invention incorporating a conical abutment.

In contrast to the prior art conventional, easily rotatable and dislodgable dental analogs, the present invention is a new analog that will not allow any rotation in the gypsum model. In a preferred embodiment, as shown in FIGS. 3 and 3A, the analog 320 of the present invention is substantially longer and has a unique feature of a transverse pin 312 or other protruding geometric shaped member extending through hole 314 in its side.

Figure 3A:
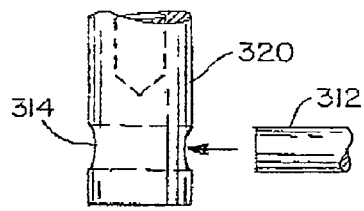
FIG. 3A is a partial view taken within the phantom circle of FIG. 3, shown rotated ninety degrees for clarity.
Figure 4:
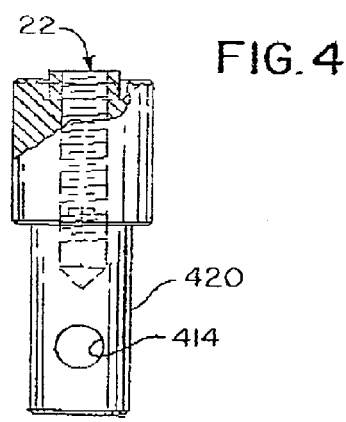
FIG. 4 is a view of an embodiment of the present invention incorporating a standard abutment.

FIG. 4 shows analog 420 with abutment 22 and hole 414 for insertion of a pin therein, similar to pin 312 of FIG. 3A.

Figure 5:
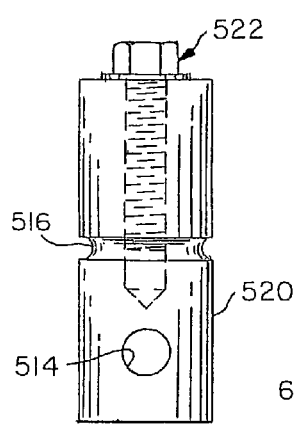
FIG. 5 is a view of an embodiment of the present invention corresponding to an implant with a hexagonal protrusion.
Figure 6:
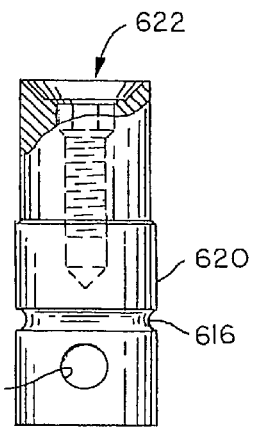
FIG. 6 is a view of an embodiment of the present invention corresponding to a large diameter implant with a hexagonal recess.
Figure 7:
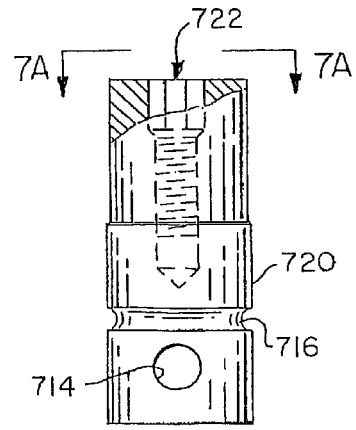
FIG. 7 is a side elevation view in partial cross section of an embodiment of the present invention corresponding to an implant with a hexagonal recess.
Figure 7A:
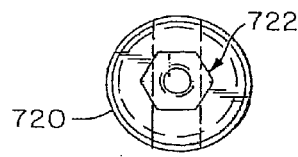
FIG. 7A is a top plan view thereof.

As shown in FIGS. 5, 6, and 7, these dental analogs 520, 620 and 720 of the present invention are preferably ridged with annular recesses, these dental analogs 520, 620 and 720 on their respective sides to gain better retention inside the gypsum model.

Analogs 420, 520, 620 and 720 have respective pins (not shown) similar to transverse pin 312 of analog 320 of FIG. 3A. These pins 312 are located at the base of the respective analogs 320, 420, 520, 620 and 720 to lock the position. These transverse pins 312 prevent horizontal, vertical or cylindrical movement of the analogs 320, 420, 520, 620, and 720 within the model.

Figure 28:
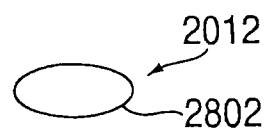
FIG. 28 depicts a cross-sectional view of a protrusion in an analog having a substantially oval shape 2802.
Figure 29:
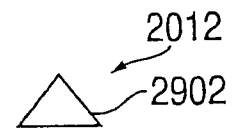
FIG. 29 depicts a cross-sectional view of a protrusion in an analog having a substantially triangular shape.
Figure 30:
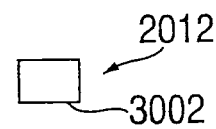
FIG. 30 depicts a cross-sectional view of a protrusion in an analog having a substantially square shape.
Figure 31:
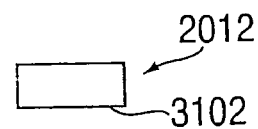
FIG. 31 depicts a cross-sectional view of a protrusion in an analog having a substantially rectangular shape; and, FIG. 32 depicts a cross-sectional view of a protrusion in an analog having a substantially hexagonal shape 3202.
Figure 32:
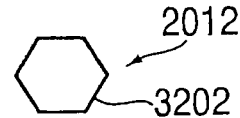

Conventional implants have a standardized system of heights, measurements and dimension for implants and abutments. The respective inventive analogs 320, 420, 520, 620, 720 of the present invention can have a shape which incorporates a conical abutment 322 (FIGS. 3 and 3A), a standard abutment 422 (FIG. 4), a hexagonal protrusion 522 (FIG. 5), a large hexagonal recess 622 (FIG. 6) or a hexagonal recess 722 (FIG. 7), as these terms are used in the dental industry. For example, FIGS. 28-32 depict cross-sectional views of protrusion embodiments having various shapes. Illustratively, FIGS. 28-32 are described with respect to protrusion 2012 however that description is not intended in any way to limit the scope of the invention. For example, it is appreciated that extensions 2051 may in various other embodiments have the shapes depicted in FIGS. 28-32. FIG. 28 depicts a cross-sectional view of protrusion 2012 having a substantially oval shape 2802. FIG. 29 depicts a cross-sectional view of protrusion 2012 having a substantially triangular shape 2902. FIG. 30 depicts a cross-sectional view of protrusion 2012 having a substantially square shape 3002. FIG. 31 depicts a cross-sectional view of protrusion 2012 having a substantially rectangular shape 3102. FIG. 32 depicts a cross-sectional view of protrusion 2012 having a substantially hexagonal shape 3202.

Analogs 520, 620 and 720 also bear annular grooves 516, 616 and 716.

The analogs 320, 420, 520, 620 and 720 of the present invention are machined to specified mechanical tolerances. In particular, the internal thread of the inventive analogs are closer to the threads of actual implants and abutment. This closer approximation to the actual implants insures that the guide screw goes into the implant the same number of turns the guide screw goes into the analog, and maintains the prosthesis in the same position relative to the patient's mouth as the prosthesis had with respect to the replica. The internal or external hexagon is also closer in dimensions to the actual implant. As a result, the prosthesis will fit on the analog and on the actual implant or abutment in the manner intended.

Another complication in the construction of dental analogs is that it is often necessary to construct a large frame using soldered connections. The present methods of soldering require a duplicate model of high heat tolerance gypsum investment be made with the present day analogs. The frame is soldered on that model. The success rate of these solder connections is far lower than expected in the industry. The present invention allows a more accurate solder connection. The present invention also holds better in the invested model and keeps the analogs from moving in the model.

Example

Figure 8:
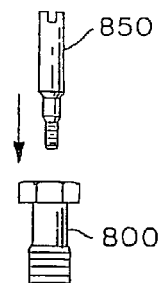
FIG. 8 shows a conventional impression coping with depth indications from 2-5 mm.

In the single tooth prosthetic work, the impression is taken from the fixture level. As shown in FIG. 8, one type of conventional impression coping 800 has an internal hexagon at the base, which corresponds to the hexagon of the abutment. The coping has depth indications for assessment of proper abutment size, 2 mm, 3 mm, 4 mm, and 5 mm. The upper margin of the abutment-like part indicates 6 mm. The impression coping is typically made of titanium.

The impression coping is used together with a special guide pin (e.g., a DCA 098), 850, for a single tooth (the guide pin used to secure the prosthesis to the implant typically has a different thread).

Typically, in the laboratory, any undercuts of the impression coping are blocked out before pouring the impression (including the depth indications). This blocking is especially important when the longest abutment is used. This precaution prevents fracturing the cast when separating the model and the impression coping.

Figure 9:
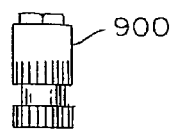
FIG. 9 shows a conventional prior art fixture replica, or analog, which is replaced by analog according to the present invention.
Figure 10:
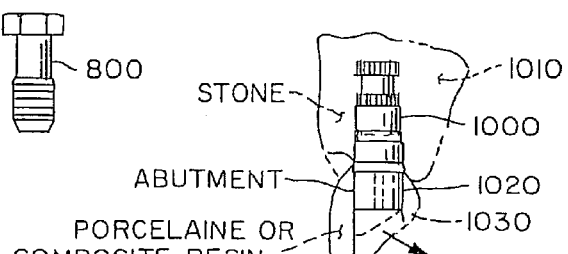
FIG. 10 shows the placement of a fixture replica, either a conventional or according to the present invention, in the lab replica that is to be secured to an abutment and a crown via a guide pin.

During the Laboratory procedure, an analog, for example a conventional prior art analog 900 shown in FIG. 9, or an analog of the present invention such as the analogs of FIGS. 3-7, is used in the laboratory jaw model, or replica, to represent the implant in the working cast. This is illustrated in FIG. 10 where analog 1000 is set in the laboratory jaw model, or replica, 1010, and the abutment 1020 and crown 1030 are secured to the jaw model by guide pin 1040. The analog has the same top hexagon and internal thread as the implant. In contrast to the stainless steel analogs of the present invention, conventionally, analogs were typically made of nickel-plated brass.

Figure 11:
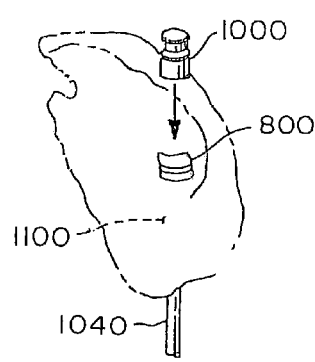
FIG. 11 shows the attachment of a fixture replica, either a conventional or according to the present invention, to an impression coping that is fixed in an impression of the relevant section of a patient's mouth prior to the casting of the lab replica.

FIG. 11 shows an impression 1100 containing an impression coping 800 being attached to an analog 1000 via guide pin 1040. Once the analog 1000 is secured to the impression coping 800 by the guide pin 1040, the impression 1100 is used to cast the laboratory jaw model, or replica, from stone, such as gypsum.

Figure 12:
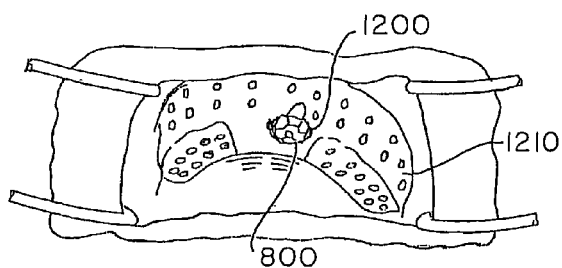
FIG. 12 shows a dental impression tray modified to provide access to the impression coping that is secured to the implant in a patient's mouth by a guide pin.
Figure 15:
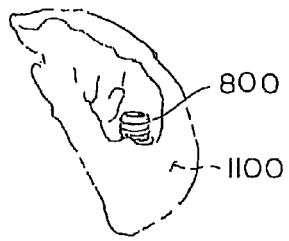
FIG. 15 shows the impression containing the impression coping.

The impression 1100 containing the impression coping 800 can be prepared in any conventional manner. For example, as shown in FIG. 12, one can make a hole 1200 in an acrylic-resin stock tray 1210 for access to the impression coping 800 which is secured to the implant by the guide screw.

Figure 13:
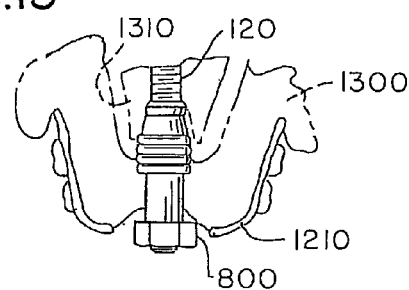
FIG. 13 shows the excess material around the impression coping in a tray containing impression material, the impression coping being secured to the implant in the patient's mouth by a guide pin.

FIG. 13 shows tray 1210 loaded with an impression material of choice 1300 in the mouth with impression coping 800 secured to implant 120 within the patient's jaw 1310.

FIG. 13 also shows the removal of any excess material around impression coping 800 once impression material 1300 has set.

Impression coping 800 is then secured to tray 1210 with auto-polymerizing acrylic resin 1400. The orientation of the hexagonal head of the implant 120 should be maintained when the impression 1100 is removed. Next, guide pin 850 is unscrewed and impression 1100 is carefully removed form the patient's mouth.

As noted before, FIGS. 3-7 show different embodiments of the dental analogs 320, 420, 520, 620 and 720 of the present invention each using a transverse rod pin 312 or tube within hole 314, 414, 514, 614, or 714, in the base section of each analog 320, 420, 520, 620, or 720 to enhance the anchoring of the analog in the plaster of the replica. Each of the different embodiments uses a different style of abutment 322, 422, 522, 622, or 722 to match that which the dentist had used in the patient's actual implant.

For example, FIG. 3 shows a conical abutment 322 for analog rod 320 and FIG. 4 shows a standard recessed abutment 422 for analog rod 420. FIG. 5 shows an abutment 522 with a hexagonal protrusion for analog rod 520, FIG. 6 shows a large diameter abutment 622 with a hexagonal recess, for analog rod 620, and FIG. 7 shows an abutment 722 with a hexagonal recess for analog rod 720.

Figure 16:
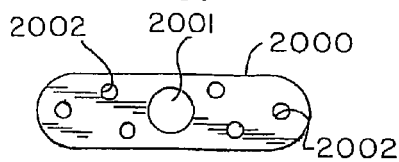
FIG. 16 is a top view of an engagement plate of this invention which is used to provide improved anchorage for a conventional analog.
Figure 14:
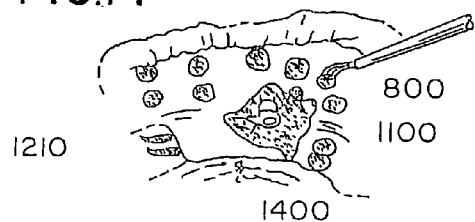
FIG. 14 shows a means of securing the impression coping to the tray containing the impression material with an acrylic resin.

FIG. 16 shows another embodiment of this invention in the form of a flat engagement plate 2000 which is used to provide enhanced anchoring of a standard prior art analog 900 (see FIG. 9) in the replica plaster.

Figure 17:
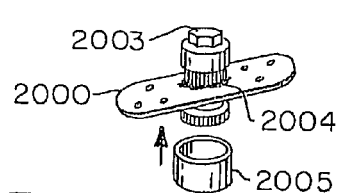
FIG. 17 is an exploded side view of the engagement plate of FIG. 16 attached to a conventional analog.

As shown in FIG. 17, the conventional analog 2003 is inserted through central hole 2001 and adhesively bonded 2004 at an oblique angle. Perforations 2002 enhance adhesion to immobilize plate 2000 in replica plaster. An optional hollow sleeve 2005 can be used to extend the vertical height of analog 2003, to further promote its anchoring within the replica plaster.

Figure 18:
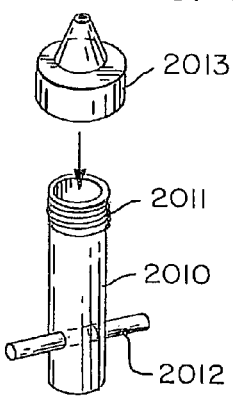
FIG. 18 is a perspective view of an analog body with a transverse tube configured to screw into a variety of abutments.
Figure 19:
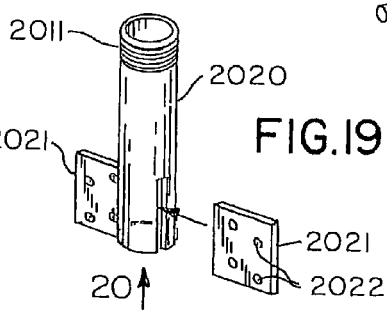
FIG. 19 is a perspective view of an analog body with transverse wings.
Figure 21:
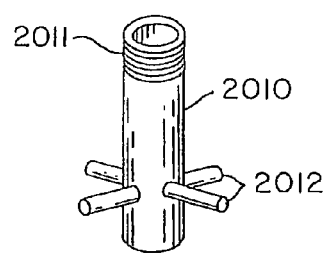
FIG. 21 is a perspective view of an analog body with coplanar transverse tubes at right angles.
Figure 23:
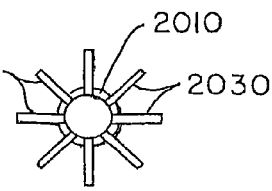
FIG. 23 is a bottom view of an analog body with eight co-planar transverse tube segments.
Figure 25:
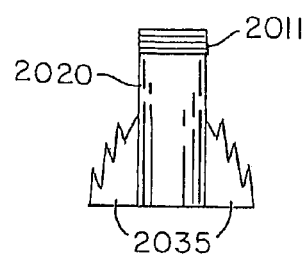
FIG. 25 is a side elevation of an analog body with serrated side extensions.
Figure 26:
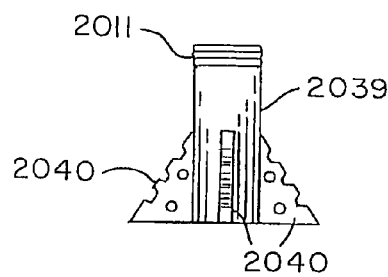
FIG. 26 is a side elevation of an analog body with four serrated and perforated side extensions.
Figure 27:
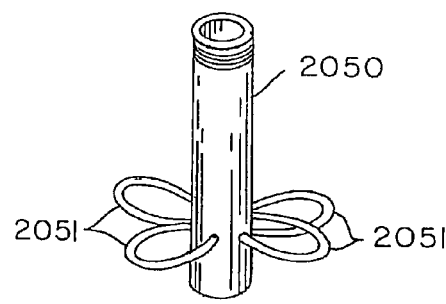
FIG. 27 is a perspective view of an analog body with looped side extensions.

It is further noted that optional removable hollow sleeve 2005 can also have any of the protrusions shown in the other drawing figures, such as protrusion rods 2012 of FIG. 18 or FIG. 21, protrusion 2022 of FIG. 19, protrusion wings 2030 of FIG. 23, protrusion barbs 2032, protrusion wings 2035 of FIG. 25, protrusion wings 2040 of FIG. 26 or protruding loops 2051 of FIG. 27.

FIG. 18 shows the concept for a series of additional embodiments of analogs of this invention which use a tubular body 2010 with external threads 2011 at the top end. These threads screw into mating female threads on a series of abutments 2013 (here illustrated as a conical abutment) which are supplied to match the style and size actually implanted in the patient's jaw.

Figure 20:
FIG. 20 is a bottom view of an analog body with transverse wings.

Therefore, analogs of this general category of embodiments can be matched with a variety of abutments 322, 422, 522, 622, or 722(as described in FIGS. 3-7). The analog 2010 with conical abutment 2013 of FIG. 18, similar to analog 320 with a conical abutment 322, uses a transverse tube or rod 2012 to aid in anchoring body 2010 in plaster. Slotted body 2020 as shown in FIG. 19 accepts two rectangular wings 2021 (as shown in bottom view of FIG. 20) with perforations 2022 as yet another embodiment to resist rotation within, and extraction from, the replica plaster.

The embodiment shown in FIG. 21 uses coplanar radial transverse tubes 2012 at right angles to each other to provide anchorage.

Figure 22:
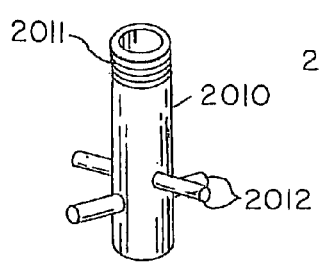
FIG. 22 is a perspective view of an analog body with non-coplanar oblique tubes.

The embodiment shown in FIG. 22 uses two oblique tubes 2012 which penetrate body 2010 as anchorage.

The bottom view of the embodiment of FIG. 23 shows eight equally spaced tubular segments 2030 attached to body 2010 to provide anchorage in replica plaster.

Figure 24:
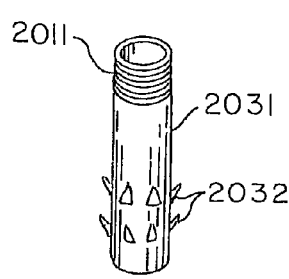
FIG. 24 is a perspective view of an analog body with angled spikes.

FIG. 24 shows an embodiment of an analog using tubular body 2031 with upward angled spikes 2032 in two rows to provide anchorage.

The embodiment of FIG. 25 shows slotted body 2020 with a pair of serrated triangular wings 2035 to provide anchorage in the replica plaster.

FIG. 26 shows an embodiment of an analog with body 2039 with four slots accommodating four perforated and serrated triangular wings 2040 to rigidly anchor it to the plaster of a replica.

Furthermore, FIG. 27 shows an embodiment of an analog using tubular body 2050 with one or more outwardly extending looped extensions 2051 to promote anchorage.

Figure 33:
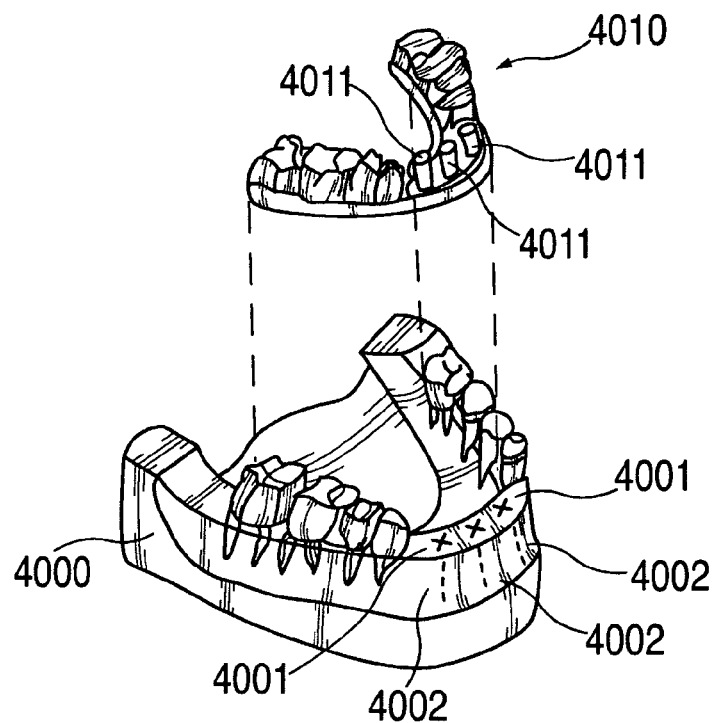
FIG. 33 is a (prior art) perspective view of a plastic resin jaw model and a surgical guide illustrating the relation between the two.
Figure 34:
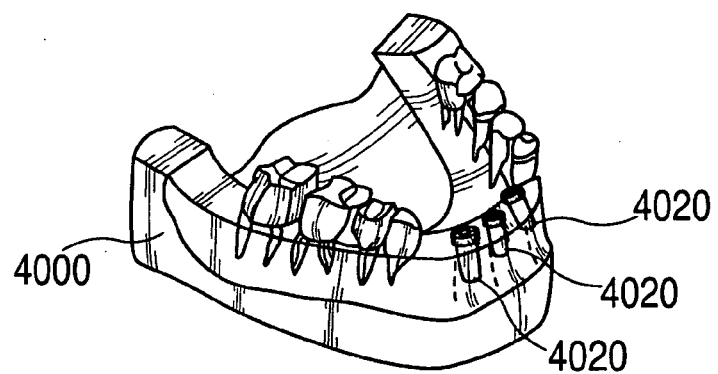
FIG. 34 is a (prior art) perspective view of a resin jaw model with analog posts installed.

FIG. 33 illustrates some features of the alternate method incorporating a resin jaw model to fabricate a prosthesis. Resin jaw model 4000 is translucent and shows teeth in a contrasting hue in the jaw. Marks 4001 placed by a dental surgeon indicate the location for the center of each analog hole to be drilled. Marks 4002 illustrate the proper angle for such analog retaining holes. Surgical guide 4010 is shown "popped-off" the teeth of jaw model 4000 over which it is formed by a thermal process. Surgical guide sleeves 4011 are shown attached at the proper angles to drill the implant post holes in the patient's jaw. Three analog posts 4020 are shown installed in jaw model 4000 in FIG. 34.

Figure 35:
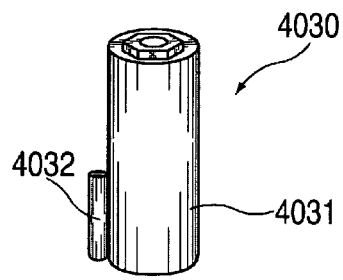
FIG. 35 is a perspective view of an analog post of this invention with a single side rod or wing attached.
Figure 36:
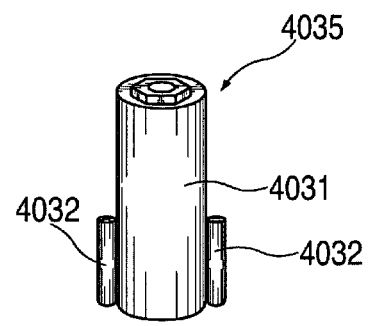
FIG. 36 is a perspective view of an analog post with two axial wings.
Figure 37:
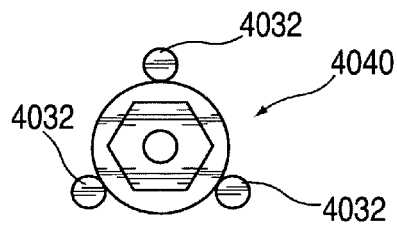
FIG. 37 is a top plan view of an analog post with three symmetrically attached side rods or wings.
Figure 38:
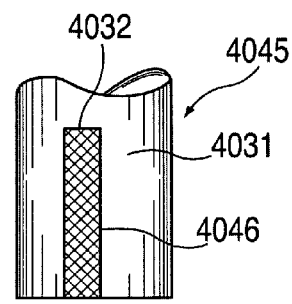
FIG. 38 is a side elevation detail showing texturing on the side of a rod or wing.
Figure 39:
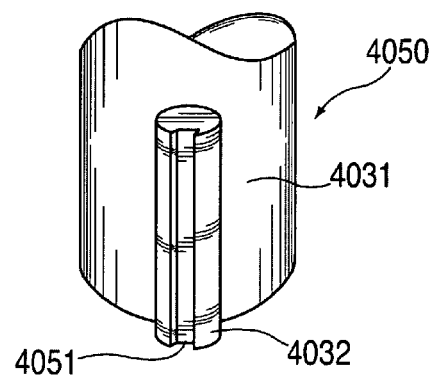
FIG. 39 is a perspective detail of showing a longitudinal groove on the side of a rod.

The analog posts in FIGS. 35-42 all have features to resist pull-out and rotation when installed in holes of a resin jaw model. FIG. 35 shows analog post 4030 with one side rod or wing 4032. FIG. 36 shows analog post 4035 with two wings 4032 attached to opposite sides of post shank 4031. FIG. 37 shows a symmetric attachment of three side wings 4032 from a top view. In all cases, these analog posts are forced inside a hole slightly smaller than would normally accommodate an analog shank with its side wings. The wings will embed into the sides of the retaining holes. FIG. 38 shows texturing 4046 as applied to outer edge of side wing 4032 to aid in retention. FIG. 39 shows groove 4051 along the length of side wing 4032 which can be used for the same purpose alternatively.

Figure 40:
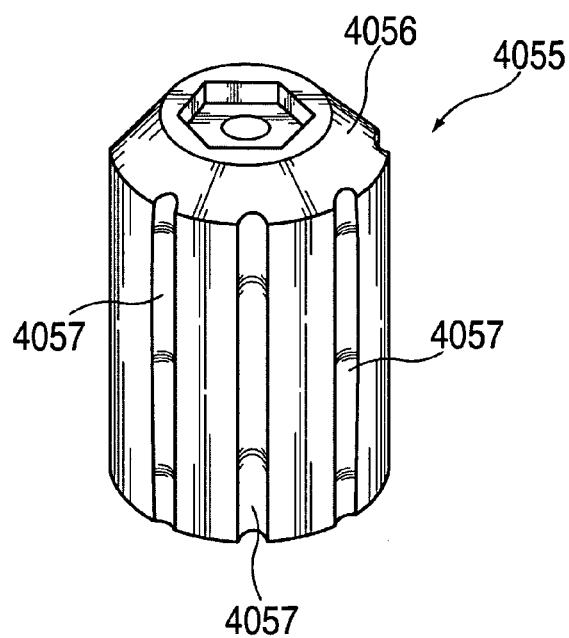
FIG. 40 is a perspective view of a fluted analog post.
Figure 41:
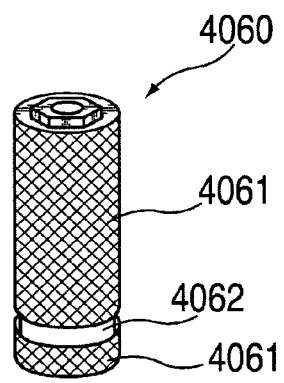
FIG. 41 is a perspective view of a knurled analog post with an annular groove adjacent the bottom end.
Figure 42:
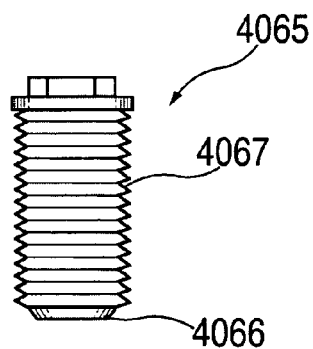
FIG. 42 is a side elevation of an analog post with male thread on its shank surface.

In lieu of side wings or attached rods, FIG. 40 shows fluted analog post 4055 with longitudinal grooves 4057 and a tapered top end 4056 which would be below the top surface of the retaining hole. FIG. 41 illustrates yet another embodiment of analog post 4060 which is knurled 4061 along its entire outer shank. An annular groove 4062 also enhances pull-out resistance. The analog post 4065 of FIG. 42 is screwed into an analog hole via tapered bottom 4066 and thread-forming male threads 4067 along its shank.

Figure 43:
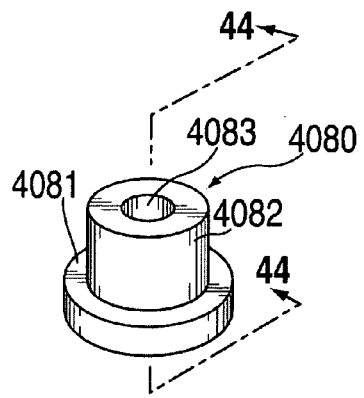
FIG. 43 is a perspective view of a cylinder sleeve support mount.
Figure 44:
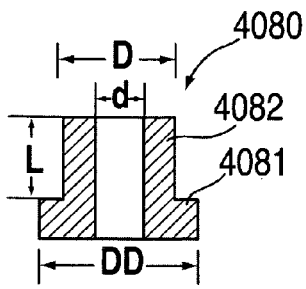
FIG. 44 is a side crossection of the mount of FIG. 43.
Figure 45:
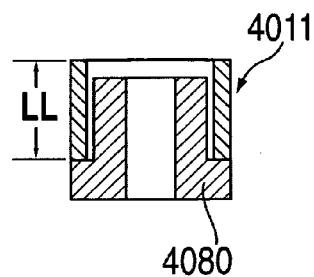
FIG. 45 is a side crossection of the cylinder sleeve support mount inside a surgical guide sleeve to show the fit of the two parts.
Figure 46:
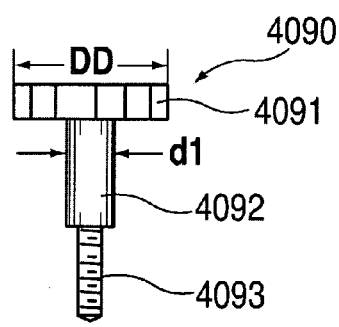
FIG. 46 is a side elevation of a retaining shoulder screw.
Figure 47:
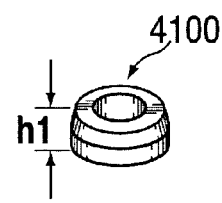
FIG. 47 is a perspective view of a short tube adapter.
Figure 48:
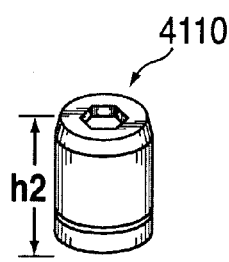
FIG. 48 is a perspective view of a medium height tube adapter.
Figure 49:
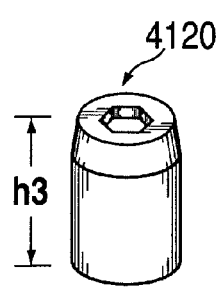
FIG. 49 is a perspective view of a larger diameter and taller tube adapter.
Figure 50:
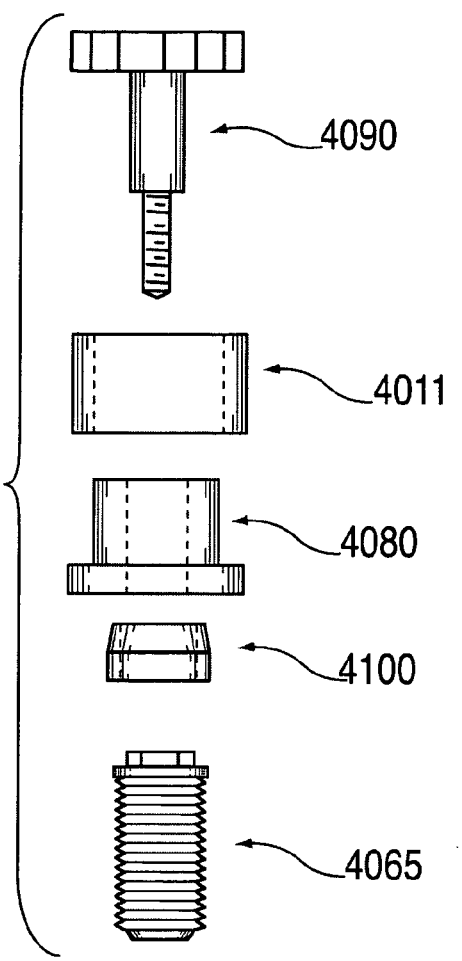
FIG. 50 is a side exploded view of the five parts from top screw to bottom analog.
Figure 51:
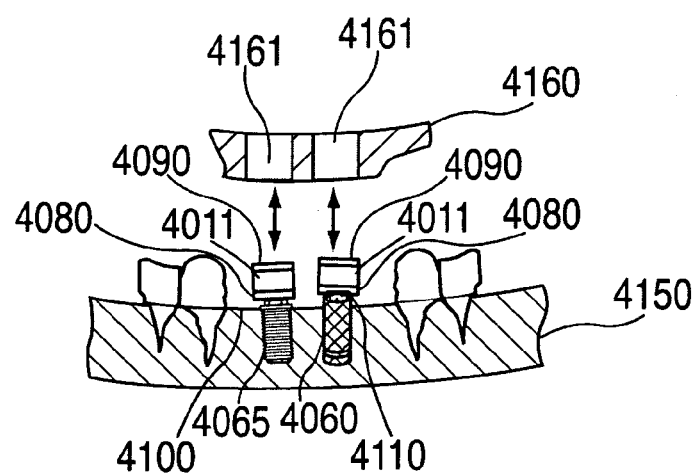
FIG. 51 is a side detail crossection of two assemblies attached to two analogs in a jaw model with a section of surgical guide in registration with the two analogs but spaced apart for clarity.

FIGS. 43-51 illustrate a presurgical method for aligning surgical guide sleeves in a surgical guide so they can be bonded in the proper orientation for use in a patient's mouth to accurately drill holes for accepting implant posts. Three parts are used for this. FIG. 43 shows a cylinder sleeve support mount 4080 with center hole 4083, shank 4082 and flange 4081. FIG. 44 shows the key dimensions of the various parts while FIG. 45 shows the fit of support mount 4080 within surgical guide sleeve 4011. The O.D. of flange 4081 (DD) matches the O.D. of guide sleeve 4011. Shank 4082 of diameter D fits in a close clearance fit inside guide sleeve 4011 which is slightly longer (LL) than height dimension L. This is to insure rigid locking by shoulder screw 4090 of FIG. 46 which has a head 4091 also of dimension DD; threads 4093 engage the central threaded hole of an analog. Note that shoulder 4092 diameter d1 is slightly smaller (close clearance fit) than hole of diameter d in support mount 4080. FIGS. 47-49 illustrate three different heights h1, h2, and h3 of tube adapters 4100, 4110, and 4120 respectively which match the outside diameter (O.D.) of an analog. Analog 4120 would be used with a larger diameter analog. Many such adapters would be made available to adjust the height of the surgical guide sleeve above the top of an analog as required. FIG. 50 shows an exploded view of the assembly of the five parts. Although analog 4065 of the screw-in variety is shown, any analog would usable with this method. Referring to FIG. 51, side crossection detail 4150 of the jaw model shows two analogs, one 4065 screw type and one knurled type 4060, rigidly installed. The method requires that the progression of parts as shown in FIG. 50 is assembled and accurately and rigidly held in place by tightening screw 4090 in each analog beneath. Note that analog 4065 has short tube adapter 4100 atop while analog 4060 uses a taller 4110 adapter. In FIG. 51, the flange portion of each cylinder sleeve support mount 4080 is visible atop the tube adapter while surgical sleeve guide 4011 is captured and guided between the head 4091 of screw 4090 and flange 4081 of mounts 4080. Note also that analogs 4065 and 4060 are tilted away from each other (not aligned) as required by the desired positioning in the jaw model. A section of surgical guide 4160 is shown above jaw model 4150 with oversize holes 4161 in registration with analogs 4065 and 4060. After the surgical guide 4160 is carefully aligned with jaw model 4150, surgical sleeve guides 4011 will be within holes 4161 where they will be bonded to surgical guide 4160. After the adhesive or cement cures, screws 4090 will be removed thereby releasing surgical guide 4160 from jaw model 4150 with surgical sleeve guides accurately attached. Analogs 4065 and 4060 will then be used by the dental lab for fabrication of appropriate prostheses. When the prostheses are made (or before), surgical guide 4160 is returned to the dental surgeon. It is used to accurately drill implant post holes in the patient's jaw using the surgical sleeve guides as drill guides to replicate the orientation of the analogs in the jaw model for a close fit of the prostheses.

Figure 52:
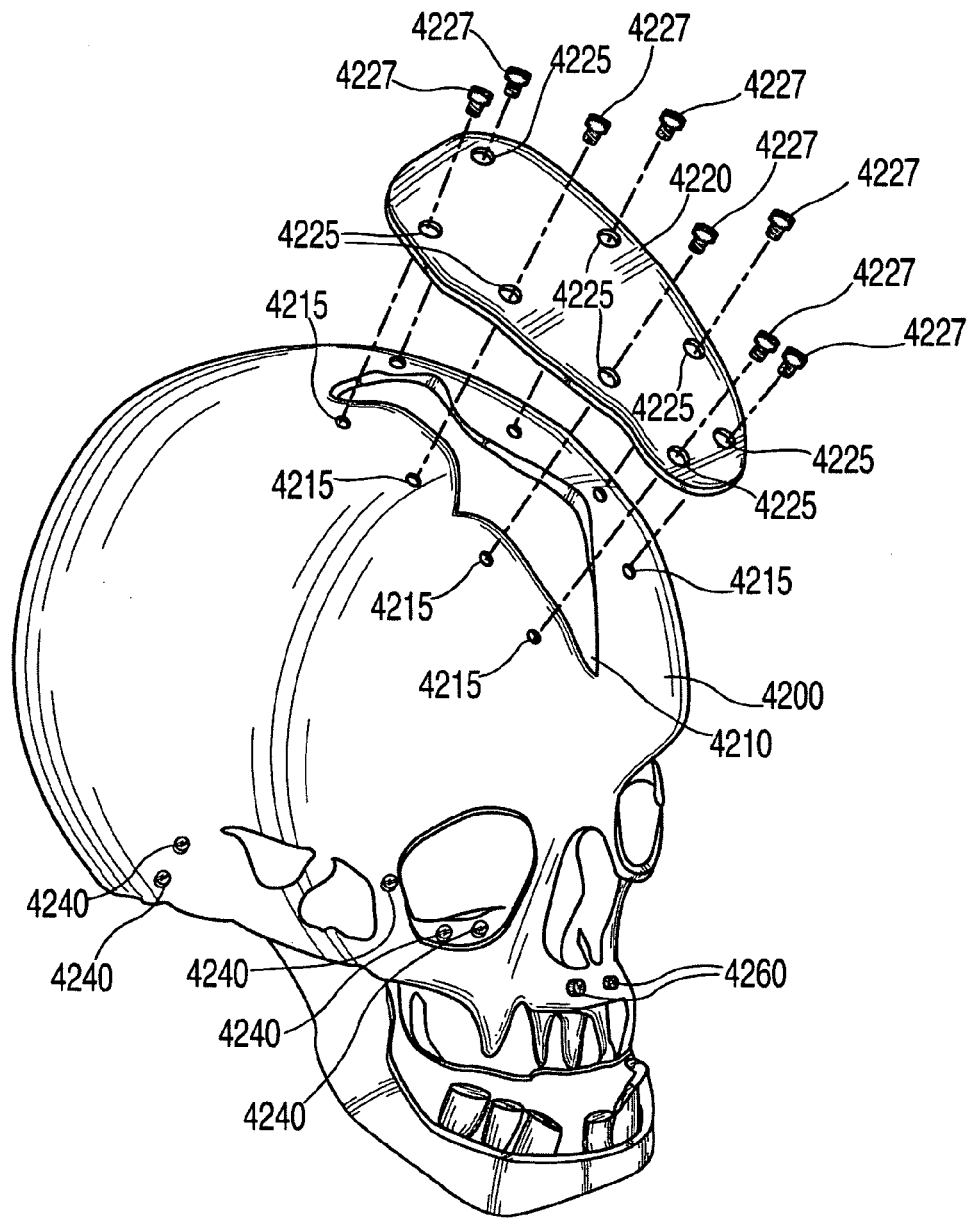
FIG. 52 is a perspective view of an accurate skull model showing analogs inserted for cranial repair, ear prosthesis, and nose prosthesis with accurate surgical guide for the cranial repair.

FIG. 52 shows a skull model 4200 which is typically created using stereolithography. Analog group 4215 (8 analogs) placed around cranial injury area 4210 will be used to plan the surgery. Also shown are a group of five analogs 4240 which will be used to attach an ear prosthesis, and a pair of analogs 4260 for a nose prosthesis. All three sites will also require accurate surgical guides for these procedures. One of these, 4220 for the cranial repair, is shown in the figure. Note the oversize holes 4215 in registration with the array of analogs 4215. Two exemplary surgical guide sleeves 4227 are shown indicating that a total of 8 such sleeves will have to be accurately bonded inside holes 4225. To facilitate this step, the parts shown in FIG. 50, namely tube adapter 4100, support mount 4080, surgical guide sleeve 4011 (4227 in FIG. 52), and screw 4090, are assembled in the order shown atop each analog 4215. Then surgical guide 4220 is placed accurately over the repair area 4210 with guide sleeves 4227 inside holes 4225. Sleeves 4227 are then bonded to guide 4220. All screws 4090 are then removed thereby releasing surgical guide 4220 with accurately bonded guide sleeves 4227; the guide sleeves will be used for drilling holes for the actual implants in the surgical procedure. Surgical guides for the ear and nose prostheses (not shown) would be similarly prepared.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention without departing from the scope of the invention, as noted in the appended Claims.

I claim:

1. A method for pre-surgical, planning for cranial and facial reconstruction of the cranium or jaw of a patient with a prosthesis attachable to the cranium or jaw of the patient with one or more attachment members comprising the steps of
   a. preparing a physical skull model made in a stereographic machine that is controlled by a computer,
      said computer using medical images of the patient for preparation of the physical skull model by the stereo a hic machine;
   b. determining a locational position and orientation for a surgical bone implant to repair missing bone in the cranium or jaw of the patient, to install an ear prostheses, and/or to install nose prostheses;
   c. using the physical skull model and preparing a surgical guide with oversize holes in registration with respective analogs for the attachment members securing surgical bone implants to be inserted to the cranium or jaw of the patient at the locational positions and orientations determined by a surgeon for the skull model, each said analog being an elongated pin with top and bottom ends, said pin having at least one anti-rotational projection extending from said pin;
   d. fitting said surgical guide atop each said elongated analog pin, and bonding a respective surgical guide sleeve for said surgical guide to the skull model at a locational position and orientation of the analog in the skull model, and;
   e. removing said surgical guide attached for accurate drilling during the surgical procedure for insertion of the implants onto the skull or jaw of patient at a location analogous to said location and orientation of said analog in said physical skull model.

2. The method for pre-surgical planning for cranial and facial reconstruction as in claim 1 wherein said at least one anti-rotational projection extends radially from said analog pin.

3. The method for pre-surgical planning for cranial and facial reconstruction as in claim 1 wherein said at least one anti-rotational projection extends parallel to an axial length of said analog pin.

4. The method for pre-surgical planning for cranial and facial reconstruction as in claim 1 wherein said surgical guide comprises an assembly. of:
   said surgical guide sleeve supported by a form-fitting cylinder support mount,
   a tube adapter to adjust the height of said surgical guide sleeve above the analog, and
   a screw threaded through said surgical guide sleeve, said form-fitting cylindrical support mount and said tube adapter from the top to secure the said surgical guide assembly to said analog below.

5. The method for pre-surgical planning for cranial and facial reconstruction as in claim 1 wherein said computer generated model is produced by the fabrication of a solid object by at least one additive method selected from the group consisting of stereolithography, laminated object manufacturing, solid freeform fabrication, and fused deposition modeling.

6. The method for pre-surgical planning for cranial and facial reconstruction as in claim 1 wherein a three dimensional shape of said computer generated skull model made in said stereographic machine is determined by computer CAD design.

7. The method for pre-surgical planning for cranial and facial reconstruction as in claim 1 wherein a three-dimensional shape of said computer generated skull model made in said stereographic machine is determined by medical images.

8. The method for pre-surgical planning for cranial and facial reconstruction as in claim 1 wherein said medical images are selected from the group consisting of x-rays, sonograms, CT Scans, nuclear imaging and magnetic resonance MRI imaging.

* * * * *